United States Patent
Lao et al.

(10) Patent No.: US 10,549,013 B2
(45) Date of Patent: Feb. 4, 2020

(54) HYBRID MATERIAL IMPLANT HAVING VARIABLE POROSITY

(71) Applicants: Universite Clermont Auvergne, Clermont-Ferrand (FR); Centre National de la Recherche Scientifique, Paris (FR)

(72) Inventors: Jonathan Claude Alexandre Lao, Veyre-Monton (FR); Edouard Daniel Albert Jallot, Saint-Beauzire (FR); Xavier Dieudonne, Ceyrat (FR)

(73) Assignees: Universite Clermont Auvergne, Clermont-Ferrand (FR); Centre National de la Recherche Scientifique, Paris (FR)

( * ) Notice: Subject to any disclaimer, the term of this patent is extended or adjusted under 35 U.S.C. 154(b) by 72 days.

(21) Appl. No.: 15/514,724

(22) PCT Filed: Sep. 28, 2015

(86) PCT No.: PCT/IB2015/057420
§ 371 (c)(1),
(2) Date: Jul. 14, 2017

(87) PCT Pub. No.: WO2016/051326
PCT Pub. Date: Apr. 7, 2016

(65) Prior Publication Data
US 2017/0348462 A1    Dec. 7, 2017

(30) Foreign Application Priority Data
Sep. 29, 2014 (FR) .................................... 14 59209

(51) Int. Cl.
*A61L 27/44* (2006.01)
*A61L 27/56* (2006.01)

(52) U.S. Cl.
CPC ............ *A61L 27/446* (2013.01); *A61L 27/56* (2013.01); *A61L 2400/08* (2013.01); *A61L 2430/02* (2013.01)

(58) Field of Classification Search
None
See application file for complete search history.

(56) References Cited

U.S. PATENT DOCUMENTS

| 4,000,525 A | * | 1/1977 | Klawitter | A61F 2/30767 264/44 |
| 5,981,827 A | * | 11/1999 | Devlin | C04B 41/85 623/23.51 |
| 7,332,452 B2 | * | 2/2008 | Ogawa | A61L 27/10 501/1 |

FOREIGN PATENT DOCUMENTS

WO    2013/023064 A2    2/2013

OTHER PUBLICATIONS

Dictionary.com definition, accessed Dec. 5, 2018 (Year: 2018).*

(Continued)

*Primary Examiner* — Robert A Wax
*Assistant Examiner* — Melissa S Mercier
(74) *Attorney, Agent, or Firm* — Morgan, Lewis & Bockius LLP

(57) ABSTRACT

The invention relates to an implant material for filling bone defects, for bone regeneration, and for bone tissue engineering, to an implant comprising said material, and to methods for manufacturing such an implant. The hybrid implant material according to the invention comprises: a biodegradable polymer P soluble in at least one solvent S1 and insoluble in at least one solvent S, different from the solvent S1; and a bioactive glass made of $SiO_2$ and $CaO$ and optionally containing $P_2O_5$ and/or optionally doped with strontium, characterized in that said implant includes a layering of a porous part having more than 90% by number (Continued)

of pores whose largest dimension is greater than or equal to 100 µm, and a dense part (2, 20, 200, 2000, 20000) having more than 80% by number of pores whose largest dimension is less than 50 µm. The invention is useful in the field of bone regeneration, particularly in the field of bone tissue engineering.

21 Claims, 9 Drawing Sheets

(56) References Cited

OTHER PUBLICATIONS

Rodenas-Rochina et al. (Comparative Study of PCL-HAp and PCL-bioglass composite scaffolds for bone tissue engineering; J. Mater Sci: Mater Med (2013) 24:1293-1308. (Year: 2013).*
Ródenas-Rochina et al., "Comparative study of PCL-HAp and PCL-bioglass composite scaffolds for bone tissue engineering," Journal of Materials Sciences: Materials in Medicine, 24: 1293-1308 (2013).
International Search Report issued in corresponding International Patent Application No. PCT/IB2015/057420 dated Dec. 9, 2015.

* cited by examiner

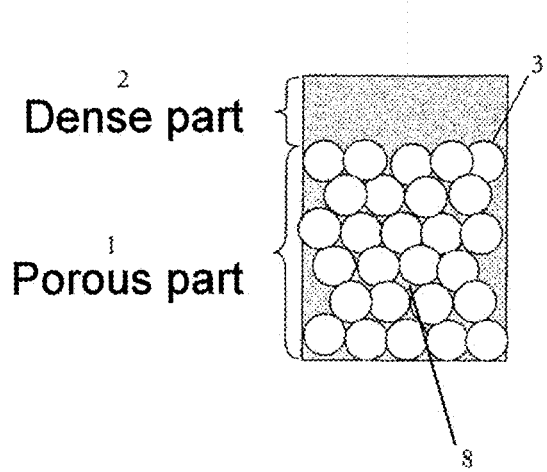
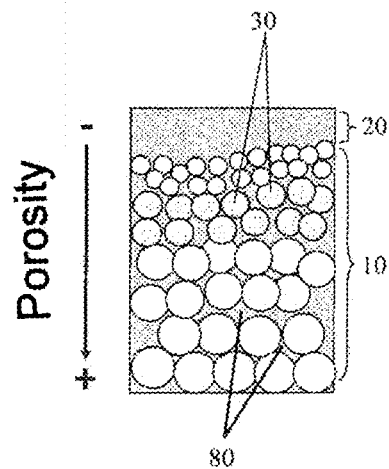
Figure 1
Figure 2
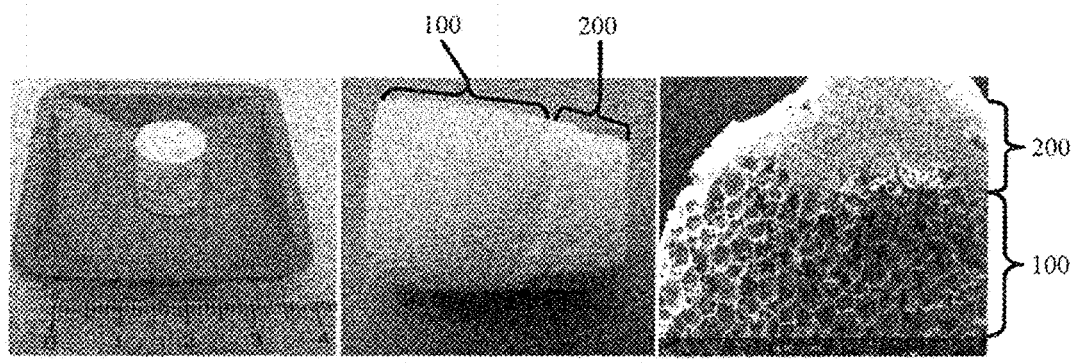
Figure 3a)
Figure 3b)
Figure 3c)

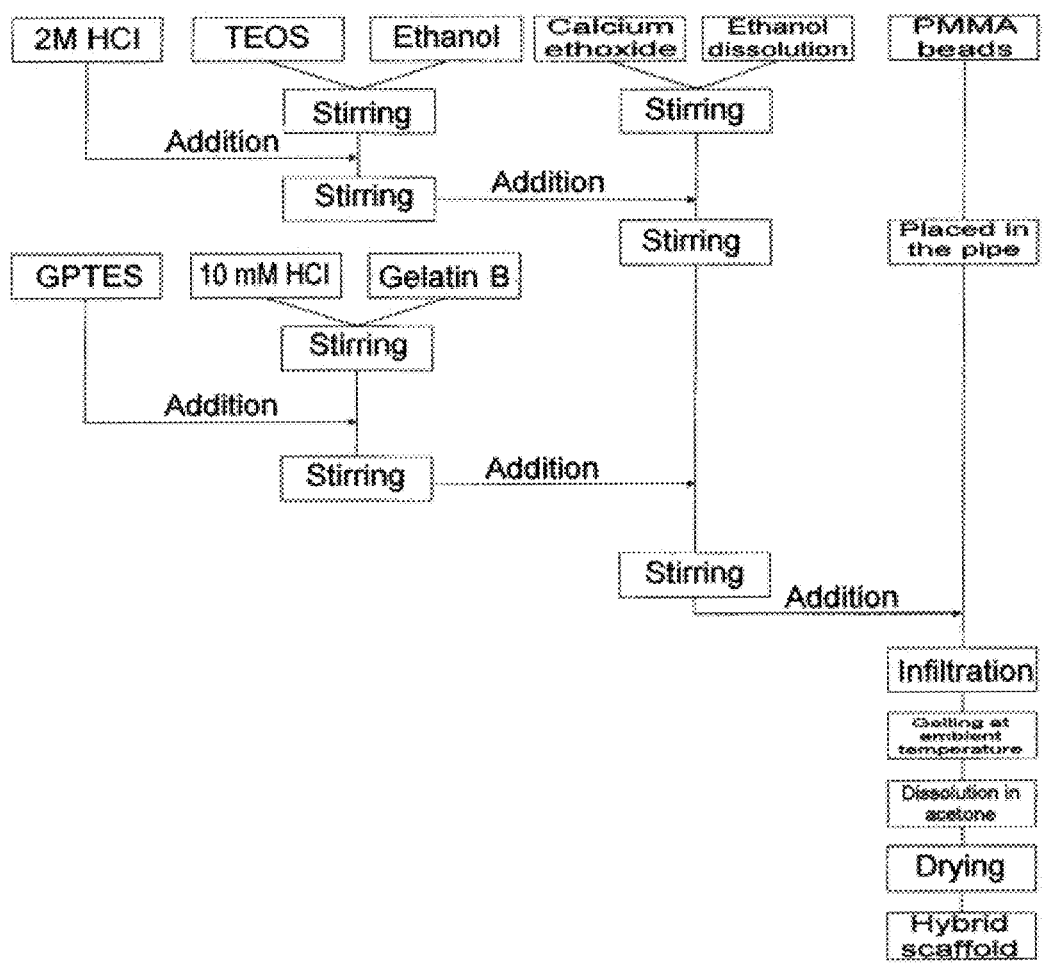
Figure 4
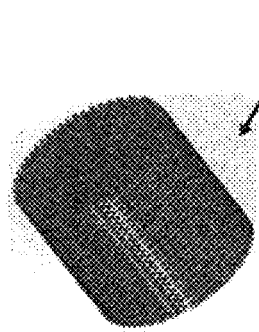 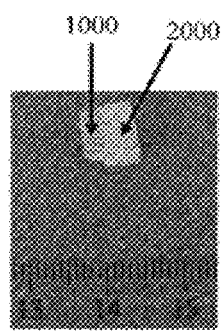 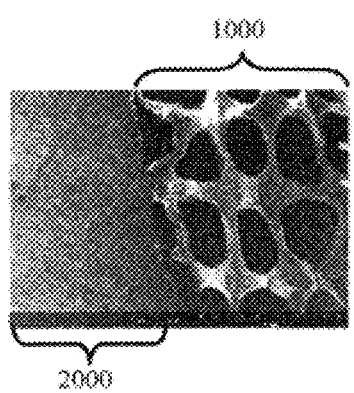
Figure 5a)   Figure 5b)   Figure 5c)

HYBRID MATERIAL IMPLANT HAVING VARIABLE POROSITY

The invention relates to an implant material for filling bone defects, for bone regeneration and for bone tissue engineering, to an implant comprising this material, and to methods for manufacturing such an implant.

The overall aging of the population and the disorders of the osteoarticular system which accompany this make it necessary to develop high-performance materials for replacing bone tissues. 18 billion euros of health care costs are in fact expended each year in France for diseases of the osteoarticular system and dental diseases; musculoskeletal disorders are the commonest occupational pathologies in industrialized countries, whereas osteoporosis develops in elderly patients; these facts delineate the contours of a major societal and economic challenge and explain the increasing demand for biomaterials, implants with increased lifetimes capable of making up for bone loss.

As recourse to grafts is limited, and materials of animal origin may pose problems of biocompatibility or risks of infection, research efforts aim to develop synthetic biomaterials capable of promoting bone regeneration.

In this case they are called bioactive implants: the material implanted is not simply intended to make up for bone loss passively, remaining as inert as possible, but on the contrary it has to stimulate and participate actively in the mechanism of bone regeneration. This is particularly important in the case of extensive bone defects, for which the self-repair mechanism no longer functions.

Currently the main bioactive materials used as bone substitutes are bioactive "ceramics", such as calcium phosphates, and bioactive glasses, also called "bioglasses".

The first bioactive ceramics were developed by L. L. Hench (L. L. Hench et al., J. Biomed. Mater. Res., 1971, 2, 117-141; L. L. Hench et al., J. Biomed. Mater. Res., 1973, 7, 25-42).

The first bioactive glasses were prepared from $SiO_2$, $P_2O_5$, $CaO$ and $Na_2O$. The oxides of silicon and of phosphorus are network formers which participate in the cohesion of the vitreous network. The alkali metals and alkaline earth metals, such as sodium and calcium, do not exhibit this capacity and modify the vitreous network by introducing chain breaks in it, which are the cause of the low melting point of these glasses, associated with increased structural disorder. Their presence results in a greater reactivity of the bioactive glasses, in particular through their corrosion in an aqueous environment. This reactivity allows formation of hydroxyapatite in the physiological medium and thus promotes bone reconstruction.

The bioglass which has received the most study is a soda-lime phosphosilicate glass called Bioglass® or Hench Bioglass. Its basic composition is 45% $SiO_2$-24.5% $CaO$-24.5% $Na_2O$-6% $P_2O_5$, by weight, with respect to the total weight of the composition. The noteworthy bioactive properties of this material require no further demonstration. Bioglass® is still one of the most advantageous bioactive (inducing a specific response from the cells) materials.

There have been numerous developments in the field of bioactive glasses since their discovery (M. Vallet-Regi et al., Eur. J. Inorg. Chem., 2003, 1029-1042), such as the incorporation of various atoms or the incorporation of active principles. The compositions of bioactive glasses have been optimized so as to promote the proliferation of osteoblasts and the formation of bone tissues (WO 02/04606). Incorporation of silver has been proposed, in particular for endowing bioactive glasses with antibacterial properties (WO 00/76486).

In its turn, the application WO 2009/027594 describes a bioactive glass in which strontium is introduced in amounts of between 0.1 and 10% of the total weight of the bioactive glass.

A characteristic feature of these bioactive materials is that they are simultaneously biocompatible, capable of binding spontaneously to bone tissues, of promoting adhesion of bone cells and, finally, of being bioresorbable, being gradually replaced with newly formed bone tissue as bone regrowth progresses.

For filling extensive bone defects, in addition to the above characteristics, the implants must have a specific morphology: the latter takes inspiration from cancellous bone, namely a highly porous structure consisting of a three-dimensional network of interconnected macropores of several hundred microns. In fact, in the case of extensive bone defects, the bone cells need an extracellular "support" matrix capable of guiding and stimulating cellular adhesion, proliferation and differentiation, while being compatible with the processes of tissue vascularization and invasion.

Such a macroporous structure is also required for the new applications envisaged in bone tissue engineering: it is a matter of manufacturing in the laboratory, starting from cells taken from the patient, new bone tissue which can later be re-implanted in the patient. For optimum execution, this tissue culture must also be supported on porous three-dimensional supports allowing good cellular adhesion, differentiation into mature cells as well as production of tissue and in particular biomineralization.

Joaquin Rodenas-Rochina et al. describe, in "Comparative study of PCL-HAp and PCL-bioglass composite scaffolds for bone tissue engineering", J. Mater. Sci. Mater. Med. (2013), 24, 1293-1308, implants made of a polymer-bioglass or polymer-hydroxyapatite composite synthetic material having such a macroporous structure.

However, implants having a mixed structure exhibiting both a dense region and a macroporous region are necessary in maxillofacial surgery and in orthopedics. For some applications, the thickness required for the dense part of the implant can be sizable, up to a thickness of several mm. Currently, only the autograft or the allograft make it possible to meet this need. They are in fact the only sources of mixed bones having sufficiently voluminous cortical parts. If the autograft is the gold standard, the low volume of removal possible with regard to the patient himself and the risk of morbidity of the donor site are serious limitations; in addition, this requires an additional surgical operation on the patient. As regards the allograft, it consists in this instance of a withdrawal of solid bone from deceased donors which is complex; the amounts of grafts available remain very limited as solid bones are tissues which are not removed very much, their morphological characteristics must correspond to those of the patient and the regulations relating to their distribution are restricting. The development of synthetic substitutes constitutes a solution to these problems.

In dental surgery, various techniques may also require implants having a mixed porous/dense structure. Among them, the guided bone regeneration technique involves physical barriers in order to prevent the colonization of the bone tissues by connective and epithelial soft tissues, thus allowing only cells having an osteogenic power to invade the healing space. Currently, resorbable or non-resorbable synthetic membranes are used to act as barrier or else to limit the resorption of a bone graft. PTFE-type non-resorbable membranes exhibit the disadvantage of having to be attached by screws and of a second operation in order to take them out, as well as the risks of exposure and infection of the membrane. Resorbable membranes are of collagen or synthetic type and, although they reduce postoperative complications, they still require a filling material supporting the membrane: see Hadi Antoun, Michel Karouni and Bouchra Sojos, La régénération osseuse guidée: résultats, limites et perspectives [Guided Bone Regeneration: Results, Limits and Prospects], Actualités Odonto-Stomatologiques, 261, 11-21, 2013.

In comparison, a single implant having a mixed porous/dense structure would exhibit the advantage of a true continuity between the porous part, which is filler-oriented, and the dense part, which acts as barrier; in addition to being resorbable, additional properties may be conferred on the dense part, such as, for example, bioactivity.

To summarize, although numerous materials and formulations have been developed for making up for bone losses, none fully meets the specifications describing the ideal implant, namely:
- to be biocompatible;
- to be bioactive: to spontaneously induce the formation of a strong interfacial bond with the bone tissues, to promote cellular activity and adhesion;
- to be bioresorbable;
- to have a suitable morphology based on a three-dimensional matrix of interconnected macropores, this three-dimensional matrix of interconnected macropores being combined with a three-dimensional matrix having only a very low number of pores;
- to have good mechanical behavior;
- to be derived from a manufacturing process allowing easy and sufficiently flexible shaping in order to fit numerous geometries of defects and making it possible to obtain two parts: a dense part and a porous part.

Suitable morphology based on a three-dimensional matrix of interconnected macropores is understood to mean that the size, the shape and the distribution of the pores as well as the size of the interconnections between these pores must be controlled.

Combination of a three-dimensional matrix of interconnected macropores and of a matrix having a low number of pores is understood to mean a matrix consisting, in all cases, of the same hybrid material, one of the parts of which comprises a three-dimensional network of interconnected micropores and the other part of which is dense.

Thus, the aim of the invention is to provide a material which responds perfectly to all these criteria and which can be manufactured by processes which make possible the production of architectures comprising a combination of porous part and of a dense part which are composed of an organic part and of an inorganic part, in the shape of a hybrid material.

To this end, the invention provides an implant material for filling bone defects, for bone regeneration and for bone tissue engineering, characterized in that it comprises a matrix made of a hybrid material comprising:
- a biodegradable polymer P soluble in at least one solvent S1 and insoluble in at least one solvent S different from the solvent S1 and a bioactive glass based on $SiO_2$ and CaO, optionally containing $P_2O_5$ and/or optionally doped with strontium, characterized in that it comprises the superimposition of:
- a porous part having more than 90% by number of pores, the greatest dimension of which is greater than or equal to 100 μm, and
- a dense part having more than 80% by number of pores, the greatest dimension of which is less than 50 μm.

Preferably, the dense part volume/porous part volume ratio is between 10/90 and 90/10.

In a first embodiment, the pores of the porous part all have the same shape and the same dimensions to within about plus or minus 10%.

Same dimensions is understood to mean that the dimensions of the pores do not vary by plus or minus 10% with respect to one another.

In a second embodiment, the porous part has pores, the greatest dimension of which decreases from the base of the implant toward the dense part.

In a third embodiment, the porous part has pores, the greatest dimension of which increases from the base of the implant toward the dense part.

In a first embodiment, the porous part and the dense part are in planar superimposition.

In a second embodiment, the porous part and the dense part are in concentric superimposition.

The pores of the porous part can have a spherical or polygonal shape, preferably the shape of squares.

The invention also provides a process for the manufacture of an implant material according to the invention having spherical pores, characterized in that it comprises the following stages:

a) selection of the alkoxide precursors of a bioactive glass M based on $SiO_2$ and CaO, optionally containing $P_2O_5$ and/or optionally doped with strontium, b) selection of a biodegradable polymer P which is soluble in at least one solvent S1 and insoluble in at least one solvent S different from the solvent S1, c) selection of microspheres of a porogenic agent A having diameters and sizes corresponding to the diameters and sizes desired for the pores in the material constituting the implant to be manufactured, this porogenic agent A being:
- made of a polymer insoluble in the at least one solvent S1 and soluble in the at least one solvent S,
- the at least one solvent S in which the material of the biodegradable polymer P is insoluble and the at least one solvent S in which the material of the porogenic agent A is soluble being identical, d) introduction of the microspheres of the porogenic agent A into a mold having the shape and the size which are desired for the implant, these microspheres forming a compact stack corresponding to the size and to the shape of the pores to be obtained for the porous part of the implant material and representing between 5% and 50% by volume, with respect to the total volume of the porogenic agent A-biodegradable polymer P-alkoxide precursors of the bioactive glass M mixture, e) introduction of the biodegradable polymer P into the alkoxide precursors of the bioactive glass M, f) introduction of the mixture obtained in stage e) into the mold, g) gelling of the mixture present in the mold after stage f), h) removal from the mold of the mixture obtained in stage g), i) removal of the microspheres of porogenic agent A by washing with the solvent S.

The invention also provides a process for the manufacture of an implant material according to the invention in which the pores can have any shape desired, including that of polygons, characterized in that it comprises the following stages:

a) selection of the alkoxide precursors of a bioactive glass M based on $SiO_2$ and CaO, optionally containing $P_2O_5$ and/or optionally doped with strontium, b) selection of a biodegradable polymer P which is soluble in at least one solvent S1 and insoluble in at least one solvent S different from the solvent S1, c) manufacture, by 3D printing, of a preform made of a polymer insoluble in the at least one solvent S1 and soluble in the at least one solvent S, this preform being the inverse replica in terms of final shape and final size which are desired for the pores in the porous part of the final implant and representing between 5% and 50% by volume of the total volume of the preform-biodegradable polymer P-alkoxide precursors of the bioactive glass M mixture, d) introduction of the preform into a mold having the shape and the size which are desired for the final implant, e) introduction of the biodegradable polymer P into the alkoxide precursors of the bioactive glass M, f) introduction of the mixture obtained in stage e) into the mold, g) gelling of the mixture present in the mold after stage f), h) removal from the mold of the mixture obtained in stage g), i) removal of the preform by washing with the solvent S.

In both these processes, stages e) and/or f) can be carried out before stage d).

However, stages d), e) and f) can also be carried out simultaneously.

In order to obtain an implant material in which the porous part and the dense part of the implant material are in planar superimposition, in stage d) the compact stack of microspheres or the preform are placed so as to touch the side walls of the mold, leaving a free space above the stack of microspheres or the preform.

In order to obtain an implant material in which the porous part and the dense part of the implant material are in concentric superimposition, in stage d) the compact stack of microspheres or the preform are placed at the center of the mold, leaving a free space between the compact stack of microspheres or the side walls of the preform and the side walls of the mold.

Preferably, the biodegradable polymer P is a biodegradable polymer soluble in at least one solvent S1 and insoluble in at least one solvent S, chosen from:

bioresorbable polysaccharides, preferably chosen from dextran, hyaluronic acid, agar, chitosan, alginic acid, sodium or potassium alginate, galactomannan, carrageenan or pectin, bioresorbable polyesters, preferably polyvinyl alcohol or poly(lactic acid):

biodegradable synthetic polymers, preferably a polyethylene glycol or poly(caprolactone), proteins, preferably gelatin or collagen, and the material of the porogenic agent or of the preform is a material chosen from biodegradable polymers insoluble in the at least one solvent S1 and soluble in the at least one solvent S, preferably chosen from poly($C_1$ to $C_4$ alkyl) methacrylates, preferably polymethyl methacrylate or polybutyl methacrylate, polyurethane, polyglycolic acid, the different forms of polylactic acids, lactic acid-co-glycolic acid copolymers, polycaprolactone, polypropylene fumarate, paraffin wax and naphthalene, or acrylonitrile/butadiene/styrene (ABS), the material of the porogenic agent A or of the preform being different from the biodegradable polymer P.

Also preferably, the biodegradable polymer P/bioactive glass M ratio by weight is between 20/80 and 80/20, limits included.

Still preferably, the bioactive glass M is a glass based on $SiO_2$ and on CaO, the biodegradable polymer P is gelatin, the material of the preform is ABS and the solvent S is acetone.

When the stack of the microspheres is used to create the pores, preferably the bioactive glass M is a glass based on $SiO_2$ and on CaO, the biodegradable polymer P is gelatin, the material of the porogenic agent A is polymethyl methacrylate and the solvent S is acetone.

The processes of the invention can additionally comprise, in stage f), a stage of introduction of a coupling agent, preferably an organoalkoxysilane compound, more preferably 3-glycidoxypropyltrimethoxysilane (GPTMS), more preferably still 3-glycidoxypropyltriethoxysilane (GPTES).

Finally, the invention provides an implant made of a hybrid material for filling bone defects, for bone regeneration and for bone tissue engineering, characterized in that it comprises an implant material according to the invention or obtained by one or other of the processes of the invention.

A better understanding of the invention will be obtained and other characteristics and advantages of the invention will become more clearly apparent on reading the explanatory description which follows and which is made with reference to the appended figures, in which:

FIG. 1 is a diagrammatic representation of an implant according to the invention, in which the porous part has pores all having the same dimension and the dense part is superimposed as a planar structure on the porous part, FIG. 2 is a diagrammatic representation of an implant according to the invention, the pores and the porous part of which exhibit a gradient of dimension of pores which decrease from the base of the implant toward the dense part of the implant, which dense part is superimposed in a planar configuration over the porous part of the implant, FIG. 3a is a photograph of an implant according to the invention in which the porous part and the dense part form a structure in planar superposition, FIG. 3b is a photograph of a section of the implant shown in FIG. 3a but seen sideways according to the invention, FIG. 3c represents a photograph, taken with an electron microscope at a magnification of ×30, of the implant represented in FIG. 3b at the interface of the porous part and of the dense part, FIG. 4 represents a flowchart of the first process for the manufacture of an implant made of a hybrid material (based on bioactive glass and on gelatin) according to the invention, FIG. 5a diagrammatically represents a preform, obtained by 3D printing, used in the second process for the manufacture of an implant made of a hybrid material according to the invention, FIG. 5b is a photograph of a section of the implant according to the invention in which the porous part and the dense part are superimposed in a planar configuration, FIG. 5c shows a photograph, taken with a scanning electron microscope at a magnification of ×30, of the implant shown in FIG. 5b at the porous part/dense part interface, FIG. 6 shows the curves of change as a function of the time of the composition (in ppm) of the physiological medium brought into contact with class-I hybrid implants made of bioactive glass/gelatin (50% ($SiO_2$—CaO)/50% gelatin) according to the invention, FIG. 7 shows the curve of change as a function of the time of the concentration (in ppm) of silicon and proteins of a physiological medium (SBF) brought into contact with class-I and class-II hybrid implants made of bioactive glass/gelatin (30% (SiO$_2$—CaO)/70% gelatin) according to the invention, FIG. 8 shows the curves of change as a function of the time of the concentration of calcium and phosphorus (in ppm) of the physiological medium (SBF) brought into contact with class-I and class-II hybrid implants made of bioactive glass/gelatin (30% (SiO$_2$—CaO)/70% gelatin) according to the invention, FIG. 9a shows a photograph of a section of an implant made of a class-I hybrid material consisting of 30% bioglass/70% gelatin B, one part of which is dense and the other part of which is porous, in planar superimposition, obtained in example 1, FIG. 9b shows a photograph, taken with a scanning electron microscope at a magnification of ×20, of a section of the hybrid implant shown in FIG. 9a, FIG. 10a shows a photograph of a section of an implant made of a class-I hybrid material consisting of 30% bioglass/70% gelatin B, one part of which is dense and the other part of which is porous, in concentric superimposition, obtained in example 2, FIG. 10b shows a view, taken with a scanning electron microscope at a magnification of ×20, of a section of the implant made of a hybrid material shown in FIG. 10a, FIG. 11a shows a photograph of a section of an implant made of a class-II hybrid material consisting of 30% bioglass/70% gelatin B, a part of which is dense and the other part of which is porous, in planar superimposition, obtained in example 3, FIG. 11b shows a photograph, taken with a scanning electron microscope at a magnification of ×20, of a section of the implant shown in FIG. 11a, FIG. 12a shows a photograph of a section of an implant made of a class-I hybrid material consisting of 30% bioglass/70% poly-D,L-lactic acid (PDLLA), a part of which is dense and the other part of which is porous, in planar superimposition, obtained in example 4, FIG. 12b shows a photograph, taken with a scanning electron microscope at a magnification of ×20, of a section of the implant shown in FIG. 12a, FIG. 13a shows a photograph of a section of an implant made of a class-II hybrid material consisting of 30% bioglass/70% polycaprolactone (PCL), a part of which is dense and the other part of which is porous, in planar superimposition, obtained in example 5, FIG. 13b shows a photograph, taken with a scanning electron microscope at a magnification of ×20, of a section of the implant made of a hybrid material shown in FIG. 13a, FIG. 14a shows a photograph of a section of an implant made of a class-I hybrid material consisting of 30% bioglass/70% PDLLA with a "random" porosity, obtained in example 6, FIG. 14b shows a photograph, taken with a scanning electron microscope at a magnification of ×20, of a section of the porous part of the implant made of a hybrid material shown in FIG. 14a, FIG. 15a shows a photograph of a section of an implant made of a class-II hybrid material consisting of 30% bioglass/70% PCL with a "random" porosity, obtained in example 7, FIG. 15b shows a photograph, taken with a scanning electron microscope at a magnification of ×20, of a section of the porous part of the implant made of a hybrid material shown in FIG. 15a, FIG. 16a shows a photograph of a section of an implant made of a class-I hybrid material consisting of 30% bioglass/70% PCL with a pore size increasing from the base of the implant toward the top of the implant, obtained in example 9, FIG. 16b shows a photograph, taken with a scanning electron microscope at a magnification of ×20, of a section of the implant made of a hybrid material shown in FIG. 16a, FIG. 17a shows a photograph of the implant obtained in example 10, FIG. 17b shows a photograph, taken with a scanning electron microscope at a magnification of ×50, of a section of the implant obtained in example 10, at the dense/porous interface, FIG. 18a shows a photograph, taken with a scanning electron microscope at a magnification of ×50, of a section of the preform used during the manufacture of the implant material obtained in example 11, FIG. 18b shows a photograph, taken with a scanning electron microscope at a magnification of ×70, of a section of the implant made of a hybrid material obtained in example 11, at the dense/porous interface, FIG. 19a shows a photograph, taken with a scanning electron microscope at a magnification of ×30, of a section of the preform used during the manufacture of the implant material obtained in example 12, FIG. 19b shows a photograph, taken with a scanning electron microscope at a magnification of ×70, of a section of the implant made of a hybrid material obtained in example 12, at the dense/porous interface, FIG. 20a shows a photograph of the implant material obtained in example 13, FIG. 20b shows a photograph, taken with a scanning electron microscope at a magnification of ×50, of a section of the implant made of a hybrid material obtained in example 13, at the dense/porous interface, FIG. 21a shows a photograph of the implant material obtained in example 14, and FIG. 21b shows a photograph, taken with a scanning electron microscope at a magnification of ×50, of a section of the implant made of a hybrid material obtained in example 14, at the dense/porous interface.

In that which precedes and that which follows, the following terms have the following meanings:
- "porous part": part of the implant material in which more than 90% by number of the pores have their greatest dimension greater than or equal to 100 μm,
- "dense part": part of the implant material in which more than 80% by number of the pores have their greatest dimension less than 50 microns,
- "interconnection(s) between pores": opening(s) making possible passage from one pore to another,
- "aqueous medium": any liquid medium containing water, or water alone,
- "biodegradable": degradable in a physiological liquid, for example a buffered saline solution (SBF),
- "bioresorbable": removable in a physiological medium containing biological cells,
- "spherical pore" or "sphere": pore or sphere, the ratio of the smallest diameter of which to the greatest diameter of which is 0.9±0.1,
- "compact stack of microspheres of porogenic agent A": stack of microspheres of porogenic agent A in which: at least 70% by number, preferably more than 95% by number, of microspheres are in contact with one another and remain in contact with one another when the porogenic agent A and biodegradable polymer P-bioactive glass M hybrid mixture is in the mold and when the stack of microspheres is covered and infiltrated with the bioactive glass M-biodegradable polymer P hybrid mixture.

It is possible to obtain such a compact stack of microspheres of porogenic agent A by centrifuging the microspheres of porogenic agent A and biodegradable polymer P-bioactive glass M hybrid mixture or else by applying a negative pressure (vacuum) or positive pressure (greater than atmospheric pressure) to the microspheres of porogenic agent A and biodegradable polymer P-bioactive glass M hybrid mixture introduced into the mold, before and during the gelling of this mixture.

The implant material for filling bone defects, for bone regeneration and for bone tissue engineering will be described in connection with FIGS. 1, 2, 3a)-3c), 5b) and 5c).

As seen in these figures, the implant material of the invention comprises a matrix comprising a porous part, denoted 1, 10, 100, 1000 and 10,000 in the figures, and a dense part, denoted 2, 20, 200, 2000 and 20,000 in the figures, referred to as "dense", that is to say in which the pores have a size of less than 50 microns.

The porous part and dense part are superimposed, one on the other or one around the other, without any substance or layer added. The material forms a single item.

The matrix of the implant material of the invention consists of an organic phase and of an inorganic phase.

The organic phase is a bioactive glass M.

Bioactive ceramics and bioactive glasses are well known to a person skilled in the art and are described in particular in L. L. Hench et al., J. Biomed. Mater. Res., 1971, 2, 117-141; L. L. Hench et al., J. Biomed. Mater. Res., 1973, 7, 25-42, for bioactive ceramics and in M. Vallet-Regi et al., Eur. J. Inorg. Chem., 2003, 1029-1042, and WO 02/04606, WO 00/76486 and WO 2009/027594, in particular. In the invention, a bioactive glass is solely used.

The organic part of the implant material of the invention is a biodegradable polymer P soluble in at least one solvent S1 and insoluble in at least one solvent S. These solvents can be water, an aqueous medium or else an organic solvent. Preferably, the biodegradable polymer P is chosen from:
  bioresorbable polysaccharides, preferably chosen from dextrin, hyaluronic acid, agar, chitosan, alginic acid, sodium or potassium alginate, galactomannan, carrageenan or pectin,
  bioresorbable polyesters, preferably polyvinyl alcohol or poly(lactic acid):
  biodegradable synthetic polymers, preferably a polyethylene glycol or poly(caprolactone), and
  proteins, preferably gelatin or collagen.

The matrix of the implant material of the invention consists of the bioactive glass M and of the biodegradable polymer P which form a hybrid material, that is to say forming a single phase.

The hybrid material used in the invention is obtained by a process which comprises the formation of a sol containing all the alkoxide precursors of the bioactive glass, the addition of the biodegradable polymer P to this sol and the gelling of the solution thus obtained by a succession of polymerization reactions (sol-gel polymerization of the inorganic phase) (condensation of the alkoxides). A hybrid mixture intimately combining the inorganic phase and the organic phase is then obtained.

The porous part 1, 10, 100, 1000 or 10,000 of the implant of the invention can have pores 3 all having the same size, that is to say pores having dimensions which do not exhibit a variation of plus or minus 10% with respect to one another, as shown in FIG. 1, or have pore sizes 30 which decrease from the bottom of the porous part up to the top of the porous part, as shown in FIG. 2, or vice versa.

However, the size of the pores can also be alternating (a row of pores with a greater diameter than the following row, and the like).

On or around this porous part 1, 10, 100, 1000, 10,000 is superimposed, in direct connection, a dense part 2, 20, 200, 2000, 20,000 consisting of the same hybrid material as the porous part 1, 10, 100, 1000, 10,000 but this time without porosity created.

Consequently, as is seen in FIGS. 1, 2, 3a, 3b, 3c and 5b and 5c, the part 2, 20, 200, 2000 can be superimposed in a planar configuration above the porous part 1, 10, 100, 1000. It can also be, as shown in FIGS. 10a and 10b, where it is denoted 20,000, placed around the porous part, denoted 10,000, forming a concentric configuration.

A first process for the manufacture of the implant of the invention is a process involving a porogenic agent A which consists of microspheres made of a polymer soluble in at least one solvent S in which the biodegradable polymer P is not for its part soluble.

Thus, the process of the invention consists in stacking microspheres of porogenic agent A made of a polymer material, different from the biodegradable polymer P, in a mold having the shape and the size corresponding to the geometry of the bone defect to be filled or of the defect where bone regeneration is desired.

These microspheres of porogenic agent A make it possible to obtain, in the end, pores for which the size and the distribution will correspond as a negative to the stack of microspheres of porogenic agent A initially produced.

This stack of microspheres of porogenic agents makes it possible to obtain the porous part 1, 10, 100, 10,000 of the implant material.

In fact, the material intended to constitute the matrix of the implant material of the invention will be subsequently be infiltrated into the stack of the beads of microspheres of porogenic agent A and also above or around this stack, then subsequently solidified in order to be able to be removed from the mold without changing the shape and the size of the stack of the desired implant. The porogenic agent A will then be removed, making it possible to obtain the implant material of the invention formed of the superimposition of a part having controlled porosity and of a dense part in which the pores have their greatest dimension less than 50 micrometers.

As is seen, this process does not use any high-temperature heat treatment to sinter the bioactive glass M, the only temperature necessary being the temperature of the evaporation of the solvent S used.

FIG. 4 shows a flowchart of this manufacturing process.

As is seen in FIG. 4, in a first stage, the porogenic agent is placed in a container of appropriate shape, corresponding to the geometry of the bone defect to be filled. The porogenic agent is placed in a stack of spheres made of a polymer material. The porogenic agent absolutely must be able to be removed without heat treatment in order to preserve the organic part of the hybrid material to be prepared. It will thus be chosen from the following list:
  poly($C_1$ to $C_4$ alkyl) methacrylates, for example: polymethyl methacrylate or polybutyl methacrylate,
  polyurethane,
  polyglycolic acid,
  the different forms of polylactic acids,
  lactic acid-co-glycolic acid copolymers,
  poly caprolactone, polypropylene fumarate,
paraffin wax and naphthalene,
acrylonitrile/butadiene/styrene (ABS).

It will be preferable to use PMMA microspheres as porogenic agent.

One of the advantages of PMMA is that it can be easily dissolved by numerous solvents. Moreover, in the case where unremoved PMMA residues were to remain, the good biocompatibility of PMMA with human tissues is a guarantee that the implant will not exhibit any risk of cytotoxicity.

In order to control the porosity and optionally to organize it, it is advantageous to use spherical particles, namely PMMA beads. Their diameter can be chosen between approximately one hundred and several hundred microns, depending on the applications.

The porosity of the material which will be finally obtained can be controlled according to three points.

First, the diameter of the pores which will be obtained depends directly on the diameter of the initial porogenic particles. It is thus sufficient to adjust the particle size of the initial PMMA beads for the purpose of very simply obtaining the desired porosity.

Secondly, the size of the interconnections between pores depends directly on the size of the contact region between the polymer beads in the initial stack. The size of this contact region can be modified by fusing together the initial polymer particles, by means of a solvent or by a preliminary heat treatment.

Thirdly, the initial organization of the porogenic beads, the greatest dimension of which is between 100 μm and 900 μm, will be carried out either randomly or in stratified fashion by size of beads but always so as to have a compact stack of beads leaving sufficient space in the mold to allow filling with a surplus of hybrid material in the sol form in order to obtain a dense part for the implant.

This initial organization of the beads can also be a compact stack of beads made of porogenic agent A, these beads all having the same shape and the same dimensions. Surplus of hybrid sol is understood to mean that the amount of hybrid sol introduced into the mold must be greater than the volume left vacant by the beads of porogenic agent (including the interstitial space accessible between these beads).

When this surplus is placed around the stack of beads, in which case the stack of beads is placed at the center of the mold in order to allow the hybrid surplus intended to form the dense part to be placed between the side walls of the mold and the side walls of the stack of beads, a concentric superimposition of the porous part and of the dense part of the implant material is obtained. When this surplus is placed above the porous part, in which case the stack of beads will be placed at the bottom of the mold with its side walls in contact with the side walls of the mold, leaving space for the surplus of hybrid sol above the stack of beads, an implant material is obtained in which the porous part and the dense part are in planar superimposition.

In a second stage, an organic/inorganic system composed of a phase made of biodegradable polymer and of a bioactive inorganic phase infiltrates the porogenic structure made of polymer; the polymer involved in the hybrid matrix and which is mixed with the bioactive glass must exhibit all the characteristics of biocompatibility and bioresorbability and be able to be easily shaped without involvement of products which may leave cytotoxic residues. This polymer will be chosen from the following list:

bioresorbable polysaccharides, for example: dextran, hyaluronic acid, agar, chitosan, alginic acid, sodium or potassium alginate, galactomannan, carrageenan or pectin, bioresorbable polyesters, for example: polyvinyl alcohol (PVA) or poly(lactic acid) (PLA), biodegradable synthetic polymers, for example: polyethylene glycol (PEG) or poly(caprolactone) (PCL), proteins, for example: gelatin or collagen.

In an embodiment of the invention, the choice of the biopolymer fell on gelatin. In fact, gelatin is a natural, biodegradable, biocompatible, inexpensive and readily available biopolymer. Gelatin is furthermore derived from the collagen naturally present in bones. Moreover, it is already used in the context of clinical applications (dressings, adhesives, encapsulation of pharmaceutical substances).

The inorganic part of the hybrid matrix for its part consists of a bioactive glass, because i) of their high ability to induce mineralization, ii) of the possibility of fashioning their textural and morphological properties (porosity, size and thus specific surface) at the nanometric scale, iii) of the wide range of bioactive compositions which it is possible to formulate, by adding thereto, for example, anti-inflammatory or osteoinducing components, iv) finally of the combination of their bioactivity and bioresorbability properties, which make them the most promising biomaterials for bone regeneration, in particular in comparison with calcium phosphates, which are generally either less bioactive or less resorbable.

According to the invention, the organic/inorganic system is produced so as to obtain a hybrid matrix. The hybrid matrix is obtained by incorporating the polymer upstream, from the process for the synthesis of the bioactive glasses, which is based on the sol-gel process. Briefly, during the sol-gel process, a solution containing all the chemical precursors of the bioactive glass is caused to gel by a succession of polymerization reactions; in our case, the biocompatible polymer (for example gelatin) is added before gelling of the sol, so as to obtain a hybrid mixture intimately combining the inorganic and organic entities. The hybrid mixture thus differs from a composite mixture by an intimate intricacy between the two organic and inorganic phases, these two phases being indiscernible (except at the molecular scale) in the case of a hybrid mixture. This is typically the case when the size domains of the organic and inorganic phases are less than a few tens of nanometers. For the production of hybrids, a major difficulty is that high- and medium-temperature (>150° C.) heat treatments are to be prohibited; in point of fact, in the normal processes, these heat treatments are essential in obtaining a homogeneous vitreous network. The invention describes here a novel synthesis route in which the synthesis is carried out at a moderate temperature (≤60° C.), close to ambient temperature. In particular, the use of an alkoxide precursor for the calcium makes possible the incorporation of this entity in the organic phase without heat treatment. This specific process is described in FIG. 4, using, in this example, a stack of PMMA beads as porogenic architecture. Once formed and before complete gelling, the hybrid mixture is poured onto the porogenic structure. Furthermore, it can be advantageous to add a coupling agent to the mixture, such as an organo-alkoxysilane; for example, the latter can be simply added to the predissolved biocompatible polymer. The role of the coupling agent is to functionalize the biocompatible polymer, for the purpose of making possible the establishment of covalent bonds with the inorganic phase (silicate network of the bioactive glass).

A true organo-inorganic copolymer is thus obtained. The advantage is to be able to control in tailor-made fashion the degradability of the hybrid implant and also its mechanical behavior, by simply varying the number of chemical bonds created between the organic and inorganic phases, this number of chemical bonds created depending on the amount of coupling agent introduced. An example of coupling agent successfully used by the inventors is GPTMS (3-glycidoxypropyltrimethoxysilane), which is soluble, for example, in an aqueous gelatin solution.

In a third stage, the container and its mixture are subjected to a gelling operation for several hours which provides the "setting" of the mixture. This operation can be carried out at a moderate temperature close to ambient temperature (≤60° C.) in order not to degrade the organic part of the hybrid.

In a fourth stage, the polymer architecture in porogenic material is removed by dissolution in an appropriate solvent.

In the examples described in FIG. 4, the PMMA beads are removed by washing with acetone. There are several advantages to the choice of acetone. First of all, the PMMA beads are easily dissolved in acetone; for its part, the gelatin is insoluble in acetone; the acetone furthermore makes it possible to continue, if necessary, the dehydration of the gelatin; finally, it is a very commonly used solvent which is relatively cheap, particularly available and recyclable and which does not exhibit a serious risk of toxicity.

After several washing stages, the initial porogenic impression is completely removed and the final hybrid material made of bioactive glass/biocompatible polymer is obtained in the form of a block which is macroporous in all or in part. Its degradability in living medium and its mechanical behavior can in addition be easily adjusted by crosslinking the biocompatible polymer during a final stage of immersion in a solution of a crosslinking agent, such as, for example, genipin, carbodiimide, glutaraldehyde or formaldehyde.

The structures obtained can be washed without any damage in ethanol baths, in order to remove possible undesirable residues (chloride, acetone, and the like).

A second process for manufacturing the implant according to the invention is based on the use of a preform, made of a polymer material, produced by 3D printing, as porogenic agent. The advantage of this process is to be able to adjust the porosity (shapes and sizes of the pores) in tailor-made fashion.

As shown in FIG. 5a, a preform made of a polymer material chosen from the same materials as those cited above as materials of the porogenic agent A, more preferably a preform made of acrylonitrile/butadiene/styrene (ABS) having a square mesh, is used in place of the PMMA beads in the flowchart shown in FIG. 4.

Thus, after the removal of the preform (9), the inverse replica of this preform is easily obtained, in this case a highly porous hybrid matrix with periodically spaced pores of perfectly controlled size and walls of even size. In the same way as above, a dense part is obtained in the implant when the container is filled not only to the level of the preform (9) but also above this preform. An implant material such as shown in FIG. 5b, having a planar structure, is then obtained.

The container can also be filled not only to the level of the preform (9) but with the preform not touching the side walls of the container and the space between the side walls of the container being filled with hybrid material alone, without porogenic agent.

An implant material having a concentric structure is then obtained.

The preform, when made with ABS, can be removed by washing with acetone.

It will be immediately understood that the material of the microspheres of the porogenic agent A and the material of the preform (9) must be different from the biodegradable polymer P used to obtain the hybrid material of the implant of the invention.

Also, the preform (9) can itself constitute the container.

In order to achieve a better understanding of the invention, the description will now be given, as purely illustrative and nonlimiting examples, of several embodiments.

EXAMPLE 1

Manufacture of an implant material according to the invention with a matrix made of hybrid material with a dense part and a porous part in planar superimposition.

The starting point was the stage of compact stacking of the microspheres of porogenic agent made of polymethyl methacrylate in a mold having the geometry desired for the implant and with a volume greater than the size of the implant. The compact stack of beads of porogenic agent represented 40% by volume, with respect to the total volume of the porogenic agent A-biodegradable polymer P-alkoxide precursors of the bioactive glass M mixture. The material of porogenic agent A was polymethyl methacrylate. The spheres had a diameter between 400 and 600 μm.

In a second stage, the hybrid mixture was poured into the mold containing the stack of beads. The volume of hybrid mixture is strictly greater than the volume left by the interstices between the beads. The volume is adjusted in order to fill the entire working volume of the mold. Thus, the volume of hybrid sol is equal to the difference between the working volume of the mold and the volume occupied by the beads.

Centrifugation or infiltration under pressure or infiltration under vacuum can be used to help the hybrid mixture to fill the interstices between the poly(methyl methacrylate) microspheres. A plug, the surface of which is flat, is placed in contact with the sol using gentle pressure with the aim of obtaining a flat surface over the implant.

The hybrid material was obtained by a sol-gel process.

In this process, a sol containing all the alkoxide precursors of the bioactive glass is caused to gel by a succession of polymerization reactions.

The alkoxide precursors were in amounts such that the composition of the bioactive glass was 75% $SiO_2$ and 25% CaO, by weight, with respect to the total weight of the bioactive glass obtained at the end.

In the case of the present example, the gelatin (the biodegradable polymer P) was added before gelling of the sol, so as to obtain a hybrid mixture.

For the preparation of hybrid material, a major difficulty is that high- and medium-temperature heat treatments, that is to say greater than 150° C., are to be avoided.

In point of fact, in the processes described in the prior art and in particular in Lin, S. et al., "Nanostructure evolution and calcium distribution in sol-gel derived bioactive glass", *Journal of Materials Chemistry*, 2009, 19, (9), 1276-1282, these heat treatments are essential for obtaining a homogeneous vitreous network, in particular for the incorporation of the calcium within the silicate network.

The use of an alkoxide precursor for the calcium makes possible the incorporation of the calcium in the inorganic phase without heat treatment.

However, the very high reactivity of calcium alkoxides with regard to the hydrolysis/condensation reactions in the presence of water means that the sol obtained is very unstable, the sol-gel polymerization taking place extremely rapidly, which to date has made it impossible to manipulate it for the purpose of producing a porous implant and has not made possible either good incorporation of the calcium in the silicate network. Thus, the inventors have discovered that, by limiting as much as possible the introduction of water into the sol and by using a different alkoxide precursor from that used in the literature (Ramila A. et al., "Synthesis routes for bioactive sol-gel glasses: alkoxides versus nitrates", *Chemistry of Materials*, 2002, 14, (12) 542-548) (namely calcium methoxyethoxide), it is possible to greatly increase the stability of the sol. The hydrolysis/condensation reactions are then sufficiently slow to make possible a homogeneous incorporation of the calcium in the silicate network, while remaining sufficiently fast to allow the polymerization of the inorganic phase. In the example, the silicon and calcium alkoxide precursors are mixed together in a slightly acidified alcoholic solution. Preferably, the alkoxide precursors are tetraethoxysilane and calcium ethoxide. Subsequently, the predissolved gelatin is added to this mixture in order to obtain a hybrid sol. Water is contributed only via the acid and the gelatin solution: this is sufficient to make possible the hydrolysis/condensation reactions while strongly limiting them, so as to have a sol which is stable and which can be manipulated for between a few minutes and a few hours, depending on the proportions of the reactants.

During the preparation of the hybrid mixture, it can be advantageous to add a coupling agent, such as an organoalkoxysilane, to the mixture.

In fact, two classes of organic-inorganic hybrid implants can be produced, depending on the nature of the interface which combines the organic component (biocompatible polymer) and the inorganic component (bioactive glass). Class I corresponds to hybrid systems in which the two components interact via weak bonds (hydrogen, Van der Waals or electrostatic bonds). In class II, in contrast, the organic-inorganic components are strongly bonded via covalent or iono-covalent bonds. This can be obtained by means of a coupling agent.

For example, the coupling agent can be simply added to the aqueous solution of the biodegradable polymer P, in this instance gelatin. The role of the coupling agent is to functionalize the gelatin, for the purpose of making possible the establishment of covalent bonds with the inorganic phase (silicate network of the bioactive glass). In the case of a composite mixture, the coupling makes it possible to obtain particles of bioactive glass bonded at the surface of the gelatin. In the case of a hybrid mixture, a true organic-inorganic copolymer (class-II hybrid) is obtained. The advantage is to be able to control in tailor-made fashion the degradability of the composite or hybrid implant and also its mechanical behavior simply by varying the number of chemical bonds created between organic and inorganic phases, this number of chemical bonds created being related to the amount of coupling agent introduced.

An example of coupling agent successfully used in the invention is GPTMS (3-glycidoxypropyltrimethoxysilane), which is soluble in an aqueous gelatin solution.

An implant material consisting of 70% by weight of gelatin and 30% by weight of bioactive glass, with a dense part representing 25% of the volume of the implant and a porous part representing 75% of the volume of the implant, was obtained.

This material is shown in FIGS. 9a and 9b.

As may be seen in FIG. 9a, the material obtained has a very even and compact size of 2 cm×0.5 cm.

As is seen in FIG. 9b, this implant consists of a dense part and of a porous part in planar superimposition.

EXAMPLE 2

Manufacture of an implant material according to the invention with a matrix made of hybrid material with a dense part and a porous part in concentric superimposition.

The starting point was the stage of a compact stacking of the microspheres of porogenic agent made of polymethyl methacrylate in a mold having the geometry desired (diameter 6 mm) for the porous part of the implant. The material of the porogenic agent A was polymethyl methacrylate. The spheres had a diameter of between 200 and 400 µm. The stack was subjected to partial fusion of the beads with an ethanol/acetone solvent mixture and with a period of time making possible the cohesion of the beads. After drying the compact stack of beads, the stack of beads is removed from the mold. We thus have a block of cohesive beads. This block is placed at the center of the mold having the geometry desired for the implant (diameter of 12 mm) and dimensions greater than the block of beads. The dimensions of this mold are suited to the total dimensions of the desired combination of the dense part and of the porous part. The block is attached to the bottom and to the center of the mold in order to prevent it from moving during infiltration.

In a second stage, the class-I hybrid mixture was poured into the mold containing the stack of beads. The volume of the beads of porogenic agent A is 20%, with respect to the total volume of the porogenic agent A-biodegradable polymer P-alkoxide precursors of the bioactive glass M mixture. Centrifugation or infiltration under pressure or infiltration under vacuum can be used to help the hybrid mixture to fill the interstices between the polymethyl methacrylate microspheres. A plug, the surface of which is flat, is placed in contact with the sol using gentle pressure with the aim of obtaining a flat surface over the implant.

The hybrid material is obtained by a sol-gel process.

In this process, a sol containing all the alkoxide precursors of the bioactive glass is caused to gel by a succession of polymerization reactions.

The alkoxide precursors were in amounts such that the composition of the bioactive glass was 75% $SiO_2$ and 25% CaO, by weight, with respect to the total weight of the bioactive glass obtained in the end. The final composition of the implant obtained was 30% bioactive glass-70% gelatin by weight, with respect to the total weight of the implant material.

In the case of the present example, the gelatin (the biodegradable polymer P) was added before gelling of the sol, so as to obtain a hybrid mixture.

The implant obtained is represented in FIGS. 10a and 10b.

As will be seen in FIG. 10a, the implant has a cylindrical shape with a dense part on the external periphery and a porous part on the internal periphery.

The implant is homogeneous and compact.

FIG. 10b clearly shows the concentric superimposition of the dense part and of the porous part which are obtained in the implant.

EXAMPLE 3

Manufacture of an implant material according to the invention with a matrix made of hybrid material, the porosity of which is "random".

The starting point was the production of a mixture of beads of different diameters. The mixture consists of 25% by weight of beads with a diameter of 100-200 μm, of 25% of beads with a diameter of 200-400 μm, of 25% of beads with a diameter of 400-600 μm and of 25% of beads with a diameter of 600-1000 μm. Subsequently, the process was continued by the stage of stacking the microspheres of polymethyl methacrylate porogenic agent in a mold having the geometry desired for the implant. The volume of the microspheres of porogenic agent A represented 50% of the total volume of the porogenic agent A-biodegradable polymer P-precursors of the bioactive glass M mixture. The material of the porogenic agent A was poly(methyl methacrylate).

In a second stage, the class-II hybrid mixture was poured into the mold containing the stack of beads. The hybrid mixture volume is such that the whole of the block of fused beads is covered. Centrifugation or infiltration under pressure or infiltration under vacuum can be used to help the hybrid mixture to fill the interstices between the polymethyl methacrylate microspheres. A plug, the surface of which is flat, is placed in contact with the sol using gentle pressure with the aim of obtaining a flat surface over the implant.

The hybrid material was obtained by a sol-gel process.

In this process, a sol containing all the alkoxide precursors of the bioactive glass is caused to gel by a succession of polymerization reactions.

The alkoxide precursors were in amounts such that the composition of the bioactive glass was 75% $SiO_2$ and 25% CaO, by weight, with respect to the total weight of the bioactive glass obtained in the end. The final composition of the implant obtained was 30% bioactive glass-70% gelatin, by weight, with respect to the total weight of the implant material.

In the case of the present example, the gelatin (the biodegradable polymer P) was added before gelling of the sol, so as to obtain a hybrid mixture.

As may be seen in FIGS. 11a and 11b, this material is an implant, the size of the pores of which varies randomly within the implant.

As is seen in FIG. 11a, the implant material of the invention forms a single item, a part of which is dense and the other part of which is porous.

The FIG. 11b is a view, taken with an electron microscope, of a section of the implant obtained in this example in which the "random" porous part and the dense part in planar superimposition are clearly distinguished.

EXAMPLE 4

Manufacture of an implant material according to the invention with a matrix made of hybrid material with a dense part and a porous part in planar superimposition in which the biodegradable polymer P is PDLLA.

The procedure as in example 1 was used, except that the gelatin was replaced with PDLLA.

The composition of the bioactive glass was 75% $SiO_2$-25% CaO, by weight, with respect to the total weight of the bioactive glass, and the final composition of the implant obtained was 30% bioactive glass-70% PDLLA, by weight, with respect to the total weight of the implant material.

The porogenic agent A was paraffin wax microspheres with a diameter of between 600 and 1000 μm. The spheres of porogenic agent A represented 40% by volume, with respect to the total volume of the porogenic agent A-biodegradable polymer P-alkoxide precursors of the bioactive glass M mixture.

The solvent S1 was tetrahydrofuran.
The solvent S was cyclohexane.

The implant obtained is shown in FIG. 12a, in which it is seen that the implant material has a size of approximately 2 cm with a porous part representing more than a third of the implant material.

FIG. 12b is a view, taken with an electron microscope, of a section of the implant obtained in this example, in which the porous part and the dense part in planar superimposition are clearly distinguished.

EXAMPLE 5

Manufacture of an implant material according to the invention with a matrix made of hybrid material with a dense part and a porous part in planar superimposition in which the biodegradable polymer P is PCL.

The procedure as in example 1 was used, except that the gelatin was replaced with PCL.

The composition of the bioactive glass was 75% $SiO_2$-25% CaO, by weight, with respect to the total weight of the bioactive glass, and the final composition of the implant obtained was 30% bioactive glass-70% PCL, by weight, with respect to the total weight of the implant material.

The porogenic agent A was paraffin wax microspheres with a diameter of between 600 and 1000 μm. The spheres of porogenic agent represented 40% by volume, with respect to the total volume of the porogenic agent A-biodegradable polymer P-alkoxide precursors of the bioactive glass M mixture.

The solvent S1 was tetrahydrofuran.
The solvent S was cyclohexane.

As may be seen in FIGS. 13a and 13b, this implant material has a porous part and a part in planar superimposition.

The implant obtained in this example is shown in FIGS. 13a and 13b.

As is seen in FIG. 13a, the implant of the invention has a dense part of even shape and a less compact porous part. It generally has a frustoconical shape.

FIG. 13b shows that a structure of the implant in which one part is dense and the other part is porous, in planar superimposition, is obtained.

EXAMPLE 6

Manufacture of an implant material according to the invention with a matrix made of hybrid material, the porosity of which is "random", in which the biodegradable polymer P is PDLLA.

The procedure as in example 3 was used, except that the gelatin was replaced with PDLLA.

The composition of the bioactive glass was 75% $SiO_2$-25% CaO, by weight, with respect to the total weight of the bioactive glass, and the final composition of the implant obtained was 30% bioactive glass-70% PDLLA, by weight, with respect to the total weight of the implant material.

The porogenic agent A was paraffin wax microspheres, the diameters of which are between 100-200 μm, 200-400 μm, 400-600 μm and 600-800 μm. Each size distribution represented a fraction of 25% by weight of the total weight of the beads introduced into the mold.

The spheres of porogenic agent A represented 30% by volume, with respect to the total volume of the porogenic agent A-biodegradable polymer P-alkoxide precursors of the bioactive glass M mixture.

The solvent S1 was tetrahydrofuran.

The solvent S was cyclohexane.

The implant obtained in this example is shown in FIGS. 14a and 14b.

As may be seen in FIGS. 14a and 14b, this material is an implant, the size of the pores of which varies randomly within the implant, and, as is seen in FIG. 14a, the implant material of the invention forms a single item, one part of which is dense and the other part of which is porous.

As is seen in FIG. 14b, the porosity of the porous part is random in the sense that the distribution of the pores is random.

EXAMPLE 7

Manufacture of an implant material according to the invention with a matrix made of hybrid material, the porosity of which is "random", in which the biodegradable polymer P is PCL.

The procedure as in example 3 was used, except that the gelatin was replaced with PCL.

The composition of the bioactive glass was 75% $SiO_2$-25% CaO, by weight, with respect to the total weight of the bioactive glass, and the final composition of the implant obtained was 30% bioactive glass-70% PCL, by weight, with respect to the total weight of the implant material.

The porogenic agent A was paraffin wax microspheres, the diameters of which are between 100-200 μm, 200-400 μm, 400-600 μm and 600-800 μm. Each size distribution represented a fraction of 25% by weight of the total weight of the beads introduced into the mold.

The spheres of porogenic agent A represented 50% by volume, with respect to the total volume of the porogenic agent A-biodegradable polymer P-alkoxide precursors of the bioactive glass M mixture.

The solvent S1 was tetrahydrofuran.

The solvent S was cyclohexane.

The implant obtained in this example is shown in FIGS. 15a and 15b.

As is seen in FIG. 15a, the implant material of the invention forms a single item, one portion of which is dense and the other portion of which is porous.

As is seen in FIG. 15b, the porosity of the porous part is random in the sense that the distribution of the pores is random.

As may be seen in FIGS. 15a and 15b, this material is an implant, the size of the pores of which varies randomly within the implant.

EXAMPLE 8

Manufacture of an implant according to the invention by use of a preform obtained by 3D printing.

The method of structuring by a rigid impression is employed here, a preform made of ABS being used as sacrificial impression to generate the porosity in the implant. In the example, the preform having a cylindrical geometry was manufactured by 3D printing and consisted of a regular meshing of bars made of ABS, as is visible in FIG. 5a. The preform is first introduced into a mold, followed by the hybrid sol containing the biodegradable polymer and the alkoxide precursors of the bioactive glass, the hybrid sol then filling the interstices of the preform. In this example, the biodegradable polymer was gelatin and the alkoxide precursors of the bioactive glass were tetraethyl orthosilicate and calcium ethoxide, mixed in proportions such that the composition of the bioactive glass obtained was 75% $SiO_2$-25% CaO. The final composition of the implant obtained was 30% bioactive glass-70% gelatin, by weight, with respect to the total weight of the implant material. Furthermore, a coupling agent, GPTMS, had been introduced into the hybrid sol so as to bond the organic and inorganic phases and to thus synthesize a class-II hybrid.

Centrifugation or infiltration under pressure or infiltration under vacuum can be used to help the hybrid mixture to fill the free interstices of the ABS walls of the preform.

If it is desired for the implant to have a dense part, it is necessary for the amount of hybrid sol introduced into the mold to be greater than the volume left vacant in the preform (interstitial space accessible between the ABS bars of the preform). In this case, a certain volume of hybrid sol will float above the preform; in the example, the height of the supernatant liquid was equal to the height of the preform. The volume of the preform made of ABS represented 30% of the total volume of the porogenic agent A-biodegradable polymer P-alkoxide precursors of the bioactive glass M mixture.

After complete gelling and drying at ambient temperature, the mixture is washed several times in baths of acetone, which is a solvent for ABS, in order to fully dissolve the preform without degrading the hybrid material.

As is shown in FIG. 5b and in FIG. 5c, the implant obtained is the exact inverse replica of the starting preform and consists of a meshing of regularly spaced hybrid walls made of bioglass-gelatin. In the example, the walls obtained had a mean thickness of 150 microns and their mean spacing was 450 microns but these characteristics can obviously be varied in a tailor-made fashion since they are directly dependent on the initial meshing of the preform.

FIG. 5b also shows that a dense part (2000) is successfully obtained at one of the ends of the implant.

EXAMPLE 9

Manufacture of an implant material according to the invention with a matrix made of hybrid material in which the size of the pores of the porous part increases from the base of the implant toward the top of the implant and terminates with a dense part, in which the biodegradable polymer P is PCL.

A compact stack of spheres of porogenic agent was produced in three successive operations, so as to have a stratified distribution by interval of sizes of spheres. The volume of the spheres of porogenic agent was divided into three thirds, depending on the size of the spheres. The starting point was the stage of compact stacking of the microspheres of porogenic agent made of paraffin wax with a diameter of 100-200 μm, the amount introduced representing a third of the volume of the spheres. Subsequently, spheres with a diameter of 400-600 μm, representing another third of the total volume of the spheres, were introduced above. Finally, the last third of the total volume of the spheres is added above and corresponds to spheres, the diameter of which is greater than 600 μm. The material of the porogenic agent A was paraffin wax. The combined porogenic spheres introduced represented 45% by volume, with respect to the total volume of the porogenic agent A-biodegradable polymer P-alkoxide precursors of the bioactive glass M mixture.

In a second stage, the class-I hybrid mixture of bioglass/PCL in a 30/70 ratio by weight was poured into the mold containing the stack of beads. The composition of the bioactive glass was 75% $SiO_2$-25% CaO, by weight, with respect to the total weight of the bioactive glass, and the final composition of the hybrid sol was 30% bioactive glass-70% PCL, by weight, with respect to the total weight of the hybrid sol.

The solvent S1 was tetrahydrofuran.
The solvent S was cyclohexane.
The implant obtained in this example is shown in FIGS. 16a and 16b.

As is seen in FIG. 16a, the implant material of the invention forms a single item, one part of which is dense and the other part of which is porous.

As is seen in FIG. 16b, the porosity of the porous part is gradual in the sense that the distribution of the pores increases in stratified fashion up to the dense part of the implant (gradual porosity).

As can be seen in FIGS. 16a and 16b, this material is an implant, the size of the pores of which varies gradually within the implant.

Thus, the different implant materials comprising a dense part and a porous part are obtained by virtue of the invention.

It will be clearly apparent to a person skilled in the art that these materials, although manufactured in a mold having the size and the shape of the bone defect to be filled or to be regenerated, can be machined in order to be even more precisely adjusted and that this machining stage also forms part of the process of the invention.

EXAMPLE 10

Manufacture of an implant material according to the invention with a matrix made of hybrid material with a bioglass composition of 75% $SiO_2$, 20% CaO and 5% SrO and the porosity of which is "random", in which material the biodegradable polymer P is PCL.

The procedure as in example 7 was used, except that the amounts of precursors were modified so as to obtain a bioglass composition equal to 75% $SiO_2$, 20% CaO and 5% SrO, by weight, with respect to the total weight of the bioactive glass, and the bioactive glass to polymer ratio was modified in order to obtain a 40% bioactive glass-60% PCL ratio, by weight, with respect to the total weight of the implant material. In order to produce this bioglass composition, use was made, in addition to calcium ethoxide and tetraethyl orthosilicate, of a strontium alkoxide precursor, strontium isopropoxide. The composition of the bioactive glass was 75% $SiO_2$, 20% CaO and 5% SrO, by weight, with respect to the total weight of the bioactive glass, and the final composition of the implant obtained was 40% bioactive glass-60% PCL, by weight, with respect to the total weight of the implant material.

The porogenic agent A was paraffin wax microspheres, the diameters of which are between 200-400 μm, 400-600 μm and 600-800 μm. Each size distribution represented a fraction of 33% by weight of the total weight of the beads introduced into the mold.

The spheres of porogenic agent A represented 30% by volume, with respect to the total volume of the porogenic agent A-biodegradable polymer P-alkoxide precursors of the bioactive glass M mixture.

The solvent S1 was tetrahydrofuran.
The solvent S was cyclohexane.
The implant obtained in this example is shown in FIGS. 17a and 17b.

As is seen in FIGS. 17a and 17b, the implant material of the invention forms a single item, one part of which is dense and the other part of which is porous.

As can be seen in FIG. 17b, this material is an implant, the size of the pores of which varies randomly within the implant.

EXAMPLE 11

Manufacture of an implant according to the invention by use of a preform obtained by 3D printing.

The procedure as in example 8 was used, except that the gelatin was replaced with collagen, the coupling agent GPTMS was replaced with GPTES and the preform made of ABS was replaced with a preform made of PLA.

The composition of the bioactive glass was 75% $SiO_2$ and 25% CaO, by weight, with respect to the total weight of the bioactive glass, and the final composition of the implant obtained was 30% bioactive glass-70% collagen, by weight, with respect to the total weight of the implant material.

The porogenic agent A was a preform made of PLA, the pores of which have a size of approximately 200 μm and the bars of which have a size of approximately 300 μm.

The preform A represented 40% by volume, with respect to the total volume of the porogenic agent A-biodegradable polymer P-alkoxide precursors of the bioactive glass M mixture.

FIG. 18a shows a section of the preform used during the manufacture of the implant material.

The solvent S1 was 10 mM hydrochloric acid.
The solvent S was chloroform.
The implant obtained in this example is shown in FIG. 18b.

As is seen in FIG. 18b, the implant material of the invention forms a single item, one part of which is dense and the other part of which is porous. The porous part of the implant is the inverse replica of the preform used.

EXAMPLE 12

Manufacture of an implant according to the invention by use of a preform obtained by 3D printing.

The procedure as in example 8 was used, except that the preform made of ABS was replaced by a preform made of PLA and the coupling agent GPTMS was replaced by GPTES.

The composition of the bioactive glass was 75% $SiO_2$ and 25% CaO, by weight, with respect to the total weight of the bioactive glass, and the final composition of the implant obtained was 30% bioactive glass-70% gelatin, by weight, with respect to the total weight of the implant material.

The porogenic agent A was a preform made of PLA, the pores of which have a size of approximately 300 μm and the bars of which have a size of approximately 200 μm.

The preform made of PLA represented 50% by volume, with respect to the total volume of the porogenic agent A-biodegradable polymer P-alkoxide precursors of the bioactive glass M mixture.

FIG. 19a shows a section of the preform used during the manufacture of the implant material.

The solvent S1 was deionized water.
The solvent S was chloroform.
The implant obtained in this example was shown in FIG. 19b.

As is seen in FIG. 19b, the implant material of the invention forms a single item, one portion of which is dense and the other portion of which is porous. The porous part of the implant is the inverse replica of the preform used.

EXAMPLE 13

Manufacture of an implant material according to the invention with a matrix made of hybrid material with a bioglass composition of 75% $SiO_2$, 20% CaO and 5% SrO and the porosity of which is "random", in which the biodegradable polymer P is gelatin.

The procedure as in example 3 was used, except that the amounts of precursors were modified so as to obtain a bioglass composition equal to 75% $SiO_2$, 20% CaO and 5% SrO, by weight, with respect to the total weight of the bioactive glass, and the coupling agent GPTMS was replaced by GPTES. In order to produce this bioglass composition, use was made, in addition to calcium ethoxide and tetraethyl orthosilicate, of a strontium alkoxide precursor, strontium isopropoxide. The composition of the bioactive glass was 75% $SiO_2$, 20% CaO and 5% SrO, by weight, with respect to the total weight of the bioactive glass, and the final composition of the implant obtained was 30% bioactive glass-70% gelatin, by weight, with respect to the total weight of the implant material.

The porogenic agent A was polymethyl methacrylate microspheres, the diameters of which are between 200-400 μm, 400-600 μm and 600-800 μm. Each size distribution represented a fraction of 33% by weight of the total weight of the beads introduced into the mold.

The spheres of porogenic agent A represented 50% by volume, with respect to the total volume of the porogenic agent A-biodegradable polymer P-alkoxide precursors of the bioactive glass M mixture.

The solvent S1 was deionized water.
The solvent S was acetone.
The implant obtained in this example is shown in FIGS. 20a and 20b.

Figure 6:
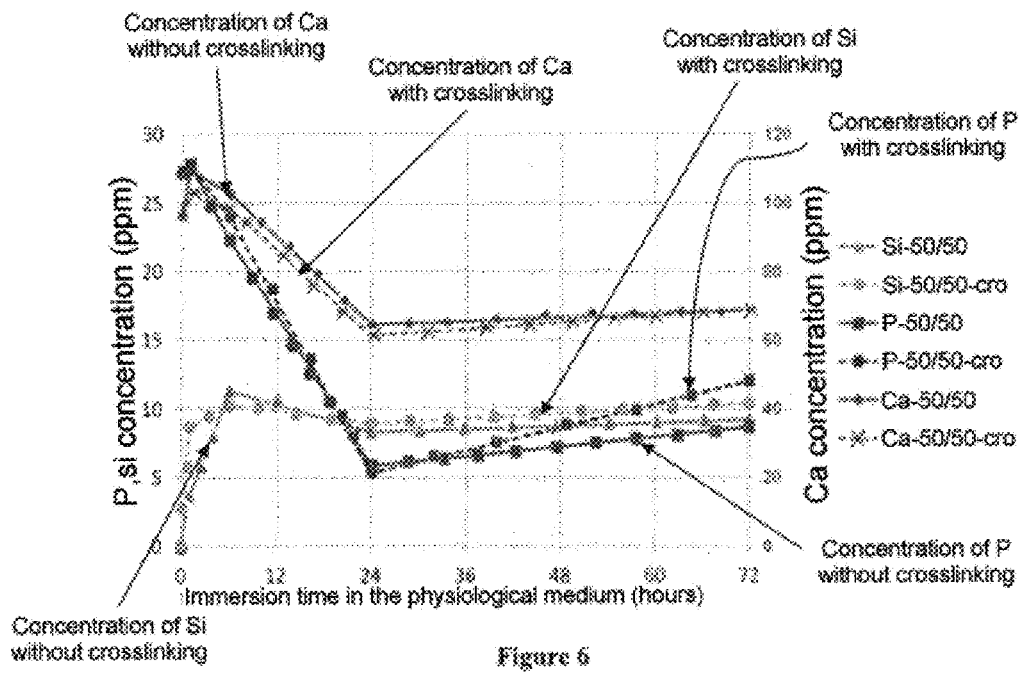
Figure 7:
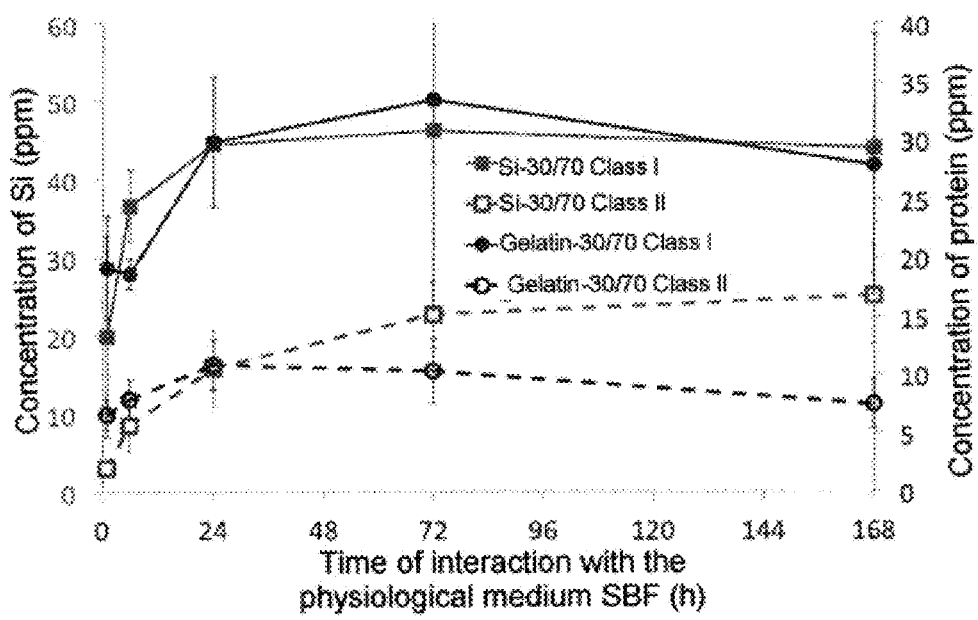
Figure 8:
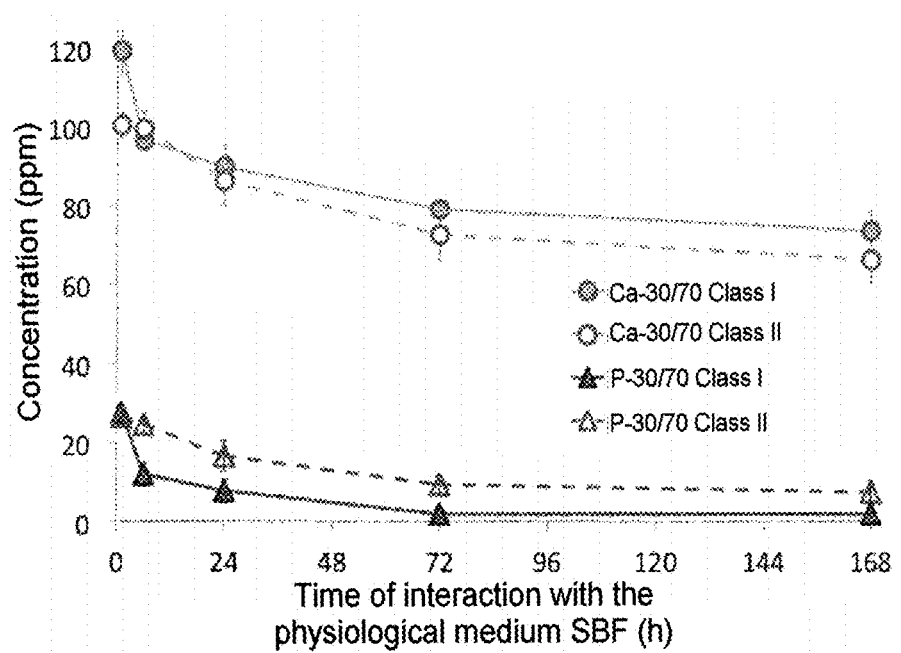
Figure 9A:
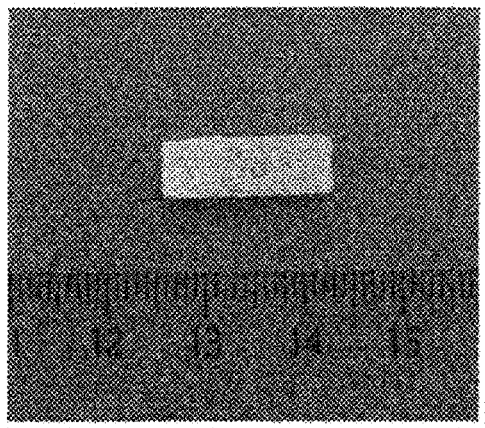
Figure 9B:
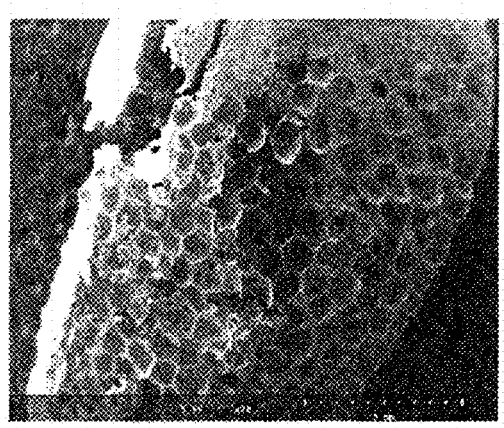
Figure 10A:
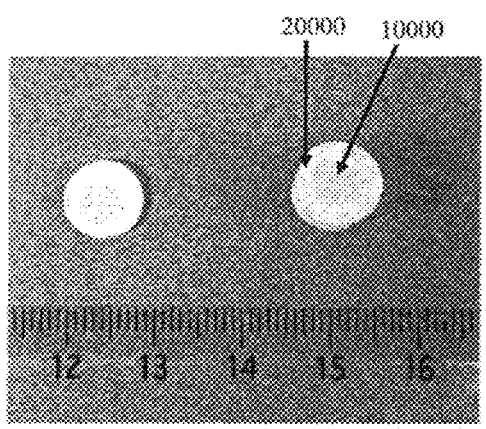
Figure 10B:
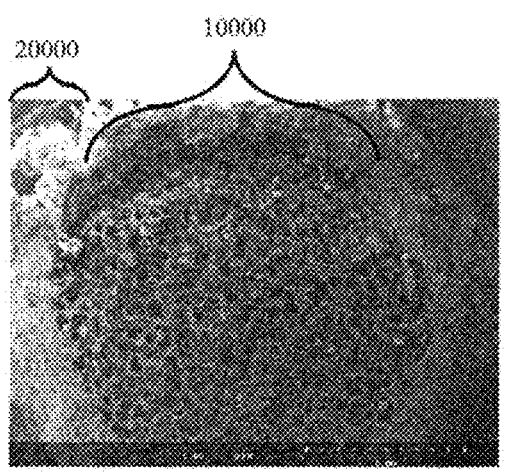
Figure 11A:
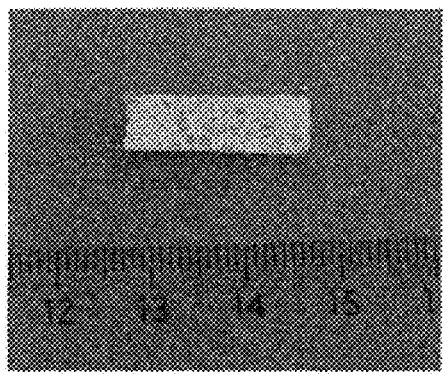
Figure 11B:
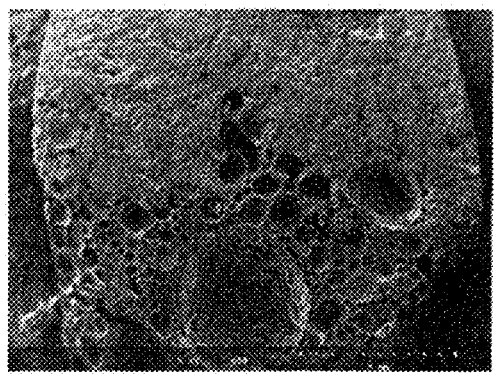
Figure 12A:
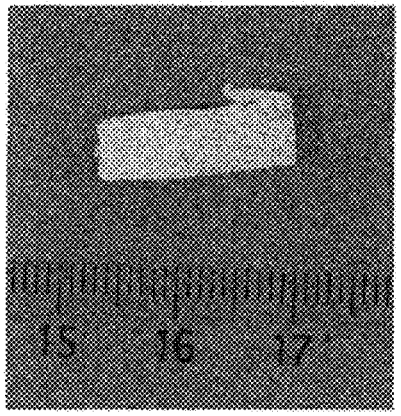
Figure 12B:
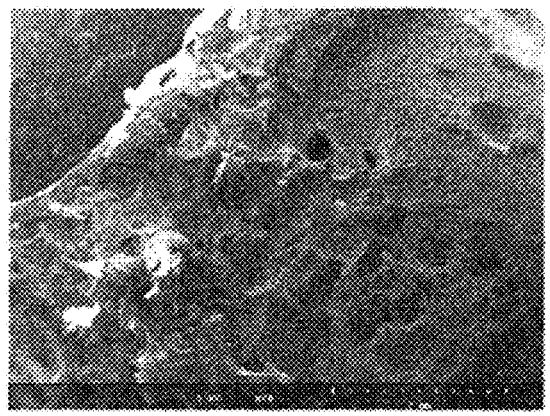
Figure 13A:
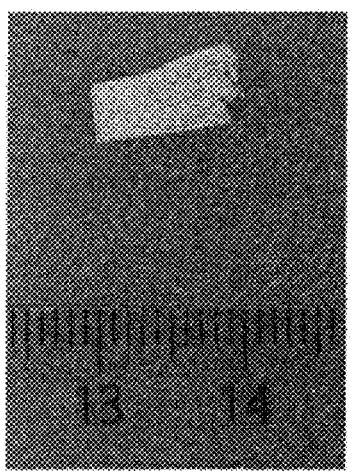
Figure 13B:
Figure 14A:
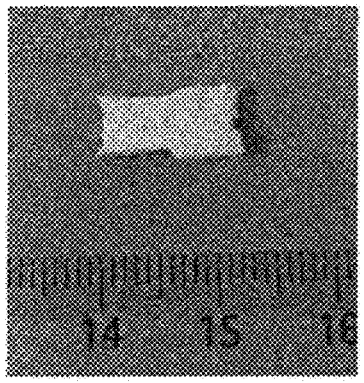
Figure 14B:
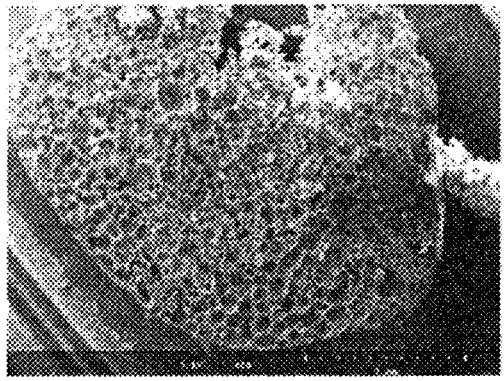
Figure 15A:
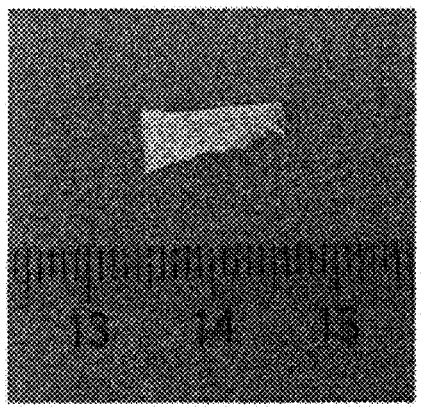
Figure 15B:
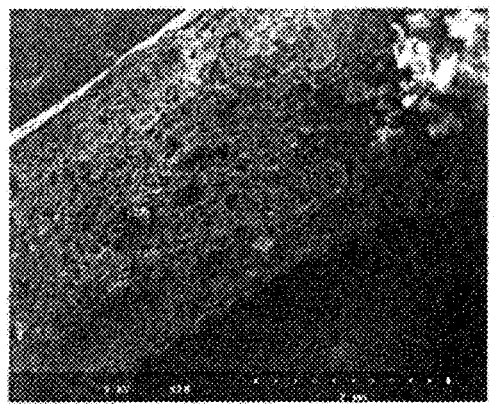
Figure 16A:
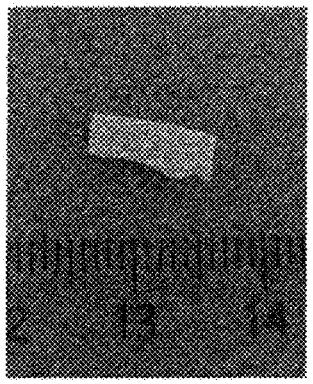
Figure 16B:
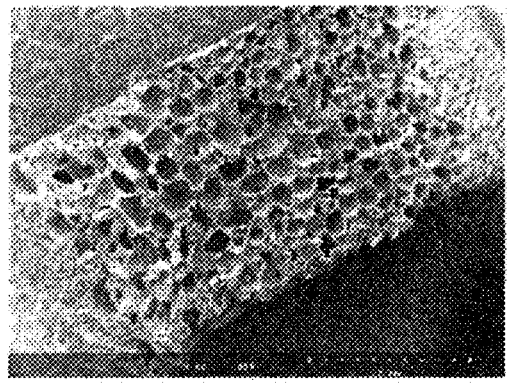
Figure 17A:
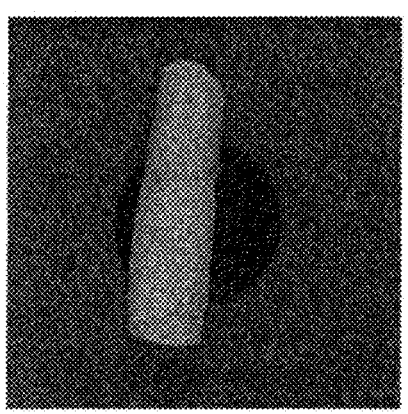
Figure 17B:
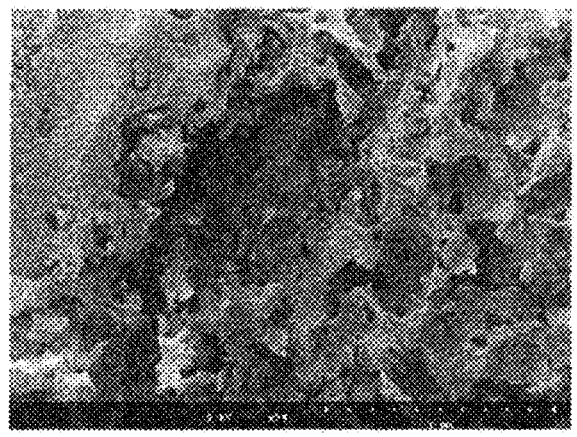
Figure 18A:
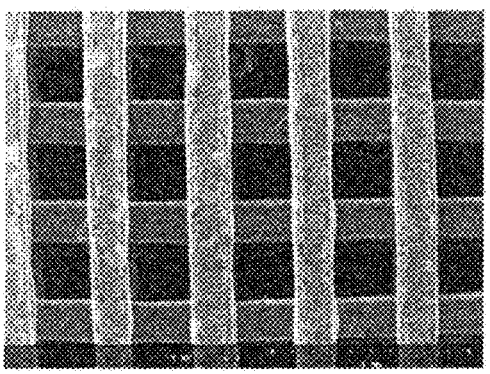
Figure 18B:
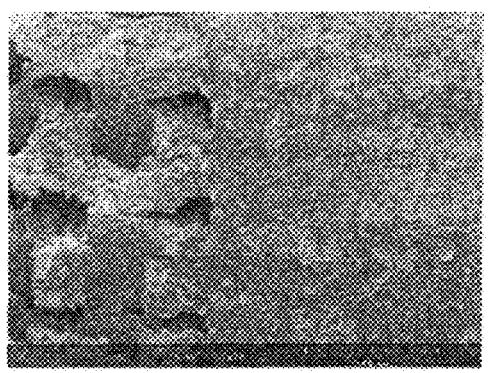
Figure 19A:
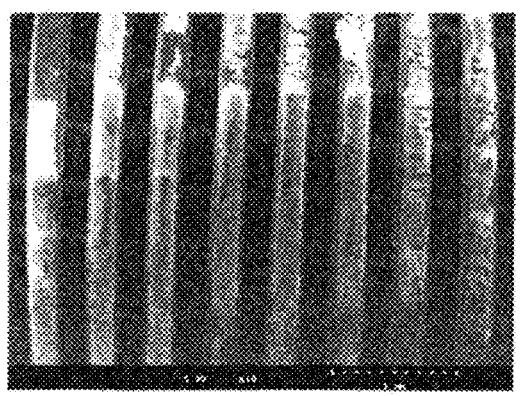
Figure 19B:
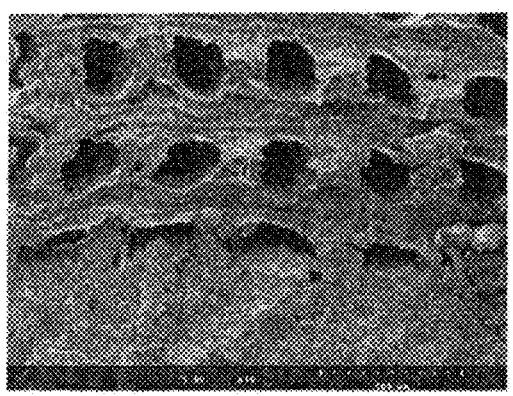
Figure 20A:
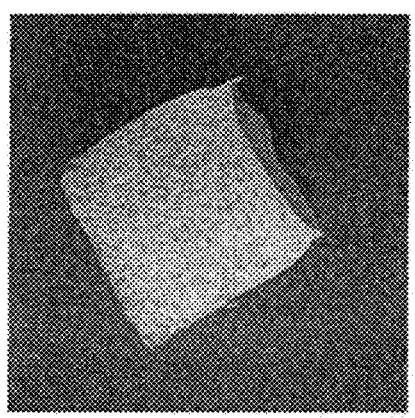
FIG. 20a shows a photograph of the implant material.
Figure 20B:
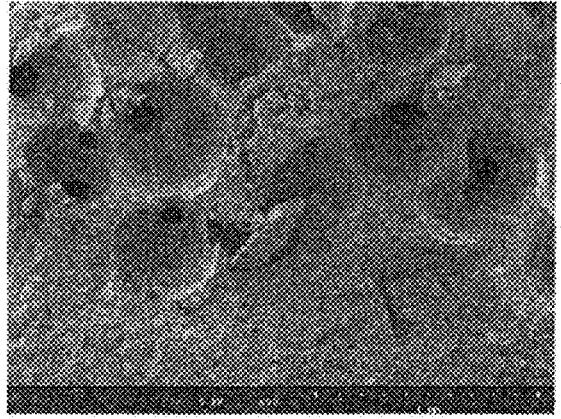
FIG. 20b shows a photograph, taken with a scanning electron microscope at a magnification of ×50, of a section of the implant made of a hybrid material, at the dense/porous interface.

As is seen in FIGS. 20a and 20b, the implant material of the invention forms a single item, one part of which is dense and the other part of which is porous.

As can be seen in FIG. 20b, this material is an implant, the size of the pores of which varies randomly within the implant.

EXAMPLE 14

Manufacture of an implant material according to the invention with a matrix made of hybrid material with a dense part and a porous part in planar superimposition, in which the biodegradable polymer P is hyaluronic acid.

The procedure as in example 1 was used, except that the gelatin was replaced by hyaluronic acid and the coupling agent GPTMS was replaced by GPTES (3-glycidoxypropyltriethoxysilane).

The composition of the bioactive glass was 75% $SiO_2$ and 25% CaO, by weight, with respect to the total weight of the bioactive glass, and the final composition of the implant obtained was 30% bioactive glass-70% hyaluronic acid, by weight, with respect to the total weight of the implant material.

The porogenic agent A was polymethyl methacrylate microspheres, the diameters of which are between 400-600 μm.

The spheres of porogenic agent A represented 40% by volume, with respect to the total volume of the porogenic agent A-biodegradable polymer P-alkoxide precursors of the bioactive glass M mixture.

The solvent S1 was deionized water.
The solvent S was acetone.

Figure 21A:
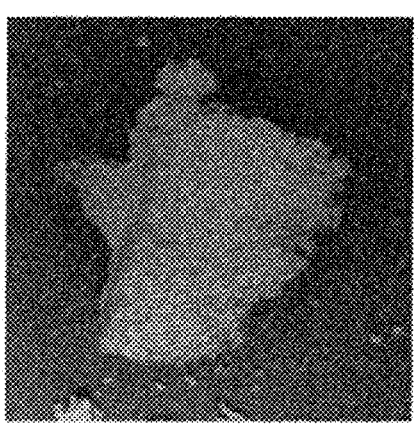
Figure 21B:
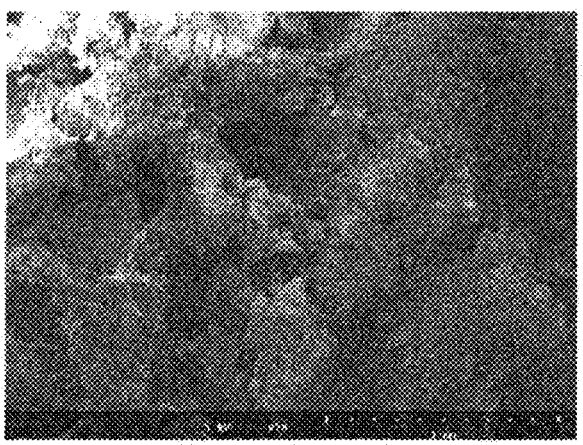

The implant obtained in this example is shown in FIGS. 21a and 21b.

As is seen in FIGS. 21a and 21b, the implant material of the invention forms a single item, one part of which is dense and the other part of which is porous.

As can be seen in FIG. 21b, this material is an implant, the size of the pores of which varies randomly within the implant.

The invention claimed is:

1. An implant material made of a hybrid material, said hybrid material comprising:
    a biodegradable polymer P soluble in at least one solvent S1 and insoluble in at least one solvent S different from the solvent S1 and a bioactive glass based on $SiO_2$ and CaO, optionally containing $P_2O_5$ and/or optionally doped with strontium,
    wherein the implant material is a unitary structure comprising:
    a porous part having more than 90% by number of pores, the greatest dimension of which is greater than or equal to 100 μm, and
    a dense part having more than 80% by number of pores, the greatest dimension of which is less than 50 μm, and
    wherein the porous part and the dense part are superimposed, one on the other in planar superimposition, without any substance or layer added between the porous part and the dense part.

2. The implant material as claimed in claim 1, wherein the dense part volume/porous part volume ratio is between 10/90 and 90/10.

3. The implant material as claimed in claim 1, wherein the pores of the porous part all have the same shape and the same dimensions.

4. The implant material as claimed in claim 1, wherein the porous part has pores, the greatest dimension of which decreases from the base of the implant toward the dense part.

5. The implant material as claimed in claim 1, wherein the porous part has pores, the greatest dimension of which increases from the base of the implant toward the dense part.

6. The implant material as claimed in claim 1, wherein the porous part and the dense part are in concentric superimposition.

7. The implant material as claimed in claim 1, wherein the pores of the porous part have a spherical shape.

8. The implant material as claimed in claim 1, wherein the pores of the porous part have the shape of polygons, preferably the shape of squares.

9. A process for the manufacture of an implant material as claimed in claim 1, wherein the process comprises the following stages:
    a) selection of the alkoxide precursors of a bioactive glass M based on $SiO_2$ and CaO, optionally containing $P_2O_5$ and/or optionally doped with strontium,
    b) selection of a biodegradable polymer P which is soluble in at least one solvent S1 and insoluble in at least one solvent S different from the solvent S1,
    c) selection of microspheres of a porogenic agent A having diameters and sizes corresponding to the diameters and sizes desired for the pores in the material constituting the implant to be manufactured, this porogenic agent A being:
        made of a polymer insoluble in the at least one solvent S1 and soluble in the at least one solvent S,
        the at least one solvent S in which the material of the biodegradable polymer P is insoluble and the at least one solvent S in which the material of the porogenic agent A is soluble being identical, d) introduction of the microspheres of the porogenic agent A into a mold having the shape and the size which are desired for the implant, these microspheres forming a compact stack corresponding to the size and to the shape of the pores to be obtained for the porous part of the implant material and representing between 5% and 50% by volume, with respect to the total volume of the porogenic agent A-biodegradable polymer P-alkoxide precursors of the bioactive glass M mixture, e) introduction of the biodegradable polymer P into the alkoxide precursors of the bioactive glass M, f) introduction of the mixture obtained in stage e) into the mold, in an amount greater than the volume left vacant by the beads of porogenic agent A, in order to obtain an implant material comprising the superimposition of a porous region and of a dense region, g) gelling of the mixture present in the mold after stage f), h) removal from the mold of the mixture obtained in stage g), i) removal of the microspheres of porogenic agent A by washing with the solvent S.

10. A process for the manufacture of an implant material as claimed in claim 1, wherein the process comprises the following stages:

a) selection of the alkoxide precursors of a bioactive glass M based on $SiO_2$ and CaO, optionally containing $P_2O_5$ and/or optionally doped with strontium, b) selection of a biodegradable polymer P which is soluble in at least one solvent S1 and insoluble in at least one solvent S different from the solvent S1, c) manufacture, by 3D printing, of a preform made of a polymer insoluble in the at least one solvent S1 and soluble in the at least one solvent S, this preform having the final shape and the final size which are desired for the pores in the porous part of the final implant and representing between 5% and 50% by volume of the total volume of the preform-biodegradable polymer P-alkoxide precursors of the bioactive glass M mixture, d) introduction of the preform into a mold having the shape and the size which are desired for the final implant, e) introduction of the biodegradable polymer P into the alkoxide precursors of the bioactive glass M, f) introduction of the mixture obtained in stage e) into the mold, in an amount greater than the volume left vacant by the preform, in order to obtain an implant material comprising superimposition of a porous region and of a dense region, g) gelling of the mixture present in the mold after stage f), h) removal from the mold of the mixture obtained in stage g), i) removal of the preform (9) by washing with the solvent S.

11. The process as claimed in claim 9, wherein stages e) and/or f) are carried out before stage d).

12. The process as claimed in claim 10, wherein stages d), e) and f) are carried out simultaneously.

13. The process as claimed in claim 9, wherein, in stage d), the compact stack of microspheres or the preform are placed so as to touch the side walls of the mold, leaving a free space above the stack of microspheres or the preform, whereby the porous part and the dense part of the implant material are in planar superimposition.

14. The process as claimed in claim 9, wherein, in stage d), the compact stack of microspheres or the preform are placed at the center of the mold while leaving a free space between the compact stack of microspheres or the side walls of the preform and the side walls of the mold, whereby the porous part and the dense part of the implant material are in concentric superimposition.

15. The process as claimed in claim 9, wherein the biodegradable polymer P is a biodegradable polymer soluble in at least one solvent S1 and insoluble in at least one solvent S chosen from:

bioresorbable polysaccharides, preferably chosen from dextrin, hyaluronic acid, agar, chitosan, alginic acid, sodium or potassium alginate, galactomannan, carrageenan or pectin, bioresorbable polyesters, preferably polyvinyl alcohol or poly(lactic acid):

biodegradable synthetic polymers, preferably a polyethylene glycol or poly(caprolactone), proteins, preferably gelatin or collagen, and in that the material of the porogenic agent or of the preform is a material chosen from biodegradable polymers insoluble in the at least one solvent S1 and soluble in the at least one solvent S, preferably chosen from poly($C_1$ to $C_4$ alkyl) methacrylates, preferably polymethyl methacrylate or polybutyl methacrylate, polyurethane, polyglycolic acid, the different forms of polylactic acids, lactic acid-co-glycolic acid copolymers, polycaprolactone, polypropylene fumarate, paraffin wax and naphthalene, or acrylonitrile/butadiene/styrene (ABS), the material of the porogenic agent A or of the preform being different from the biodegradable polymer P.

16. The process as claimed in claim 9, wherein the biodegradable polymer P/bioactive glass M ratio by weight is between 20/80 and 80/20, limits included.

17. The process as claimed in claim 10, wherein the bioactive glass M is a glass based on $SiO_2$ and on CaO, the biodegradable polymer P is gelatin, the material of the preform (9) is ABS and the solvent S is acetone.

18. The process as claimed in claim 9, wherein the bioactive glass M is a glass based on $SiO_2$ and on CaO, the biodegradable polymer P is gelatin, the material of the porogenic agent A is polymethyl methacrylate and the solvent S is acetone.

19. The process as claimed in claim 9, wherein it additionally comprises, in stage f), a stage of introduction of a coupling agent, preferably an organoalkoxysilane compound, more preferably 3-glycidoxypropyltrimethoxysilane (GPTMS), more preferably still 3-glycidoxypropyltriethoxysilane (GPTES).

20. An implant made of a hybrid material for filling bone defects, for bone regeneration and for bone tissue engineering, wherein the implant comprises an implant material as claimed in claim 1.

21. An implant made of a hybrid material for filling bone defects, for bone regeneration and for bone tissue engineering, wherein the implant comprises an implant material obtained by the process as claimed in claim 9.

* * * * *